(12) United States Patent
Ando et al.

(10) Patent No.: US 7,505,560 B2
(45) Date of Patent: Mar. 17, 2009

(54) 3-DIMENSIONAL IMAGE CONSTRUCTION METHOD AND APPARATUS

(75) Inventors: Masami Ando, Tsukuba (JP); Anton Maksimenko, Tsukuba (JP); Hiroshi Sugiyama, Tsukuba (JP); Tetsuya Yuasa, Yonezawa (JP)

(73) Assignee: High Energy Accelerator Research Organization, Tsukuba (JP)

( * ) Notice: Subject to any disclaimer, the term of this patent is extended or adjusted under 35 U.S.C. 154(b) by 0 days.

(21) Appl. No.: 11/885,069

(22) PCT Filed: Feb. 28, 2006

(86) PCT No.: PCT/JP2006/304203

§ 371 (c)(1),
(2), (4) Date: Aug. 24, 2007

(87) PCT Pub. No.: WO2006/090925

PCT Pub. Date: Aug. 31, 2006

(65) Prior Publication Data

US 2008/0170653 A1    Jul. 17, 2008

(30) Foreign Application Priority Data

Feb. 28, 2005    (JP)    ............................. 2005-053491
Sep. 2, 2005    (JP)    ............................. 2005-254990

(51) Int. Cl.
     *G21K 1/06*    (2006.01)
(52) U.S. Cl. .......................................... 378/84; 378/70
(58) Field of Classification Search ................ 378/70, 378/71, 73, 76, 82, 83, 84, 85, 87
See application file for complete search history.

(56) References Cited

U.S. PATENT DOCUMENTS 5,715,291 A * 2/1998 Momose ...................... 378/84

2002/0027970 A1 * 3/2002 Chapman et al. ............. 378/62

OTHER PUBLICATIONS

Chapman, D. et al., "Diffraction Enhanced X-Ray Imaging," Phys. Med. Biol., vol. 42, pp. 2015-2025, 1997.
Zhu, P. P. et al., "Computed Tomography Algorithm Based On Diffraction-Enhanced Imaging Setup," Applied Physics Letters, vol. 87, pp. 264101, Dec. 2005.

* cited by examiner

*Primary Examiner*—Hoon Song
(74) *Attorney, Agent, or Firm*—Oliff & Berridge, PLC

(57) ABSTRACT

A method and apparatus for constructing a 3-dimensional image of the internal organs invisible by the conventional method is provided. The apparatus comprises: generating means for generating a monochromatic and parallel X-ray beam from an X-ray beam; a reflection-type angle analyzer for reflecting the monochromatic and parallel X-ray beam at reflecting points on both slopes of a reflection curve of the reflection-type analyzer, angle information being extracted to a maximum extent at the reflecting points, the monochromatic and parallel X-ray beam including an X-ray beam which passed through the object when the object is positioned on a rotatable goniometer in the monochromatic and parallel X-ray beam and an X-ray beam from the generating means when the object is not positioned in the monochromatic and parallel X-ray beam; an imaging device for generating a refraction angle data by receiving the monochromic and parallel X-ray beam reflected on the reflection-type angle analyzer to detect the intensity thereof, and output a refraction angle data; and
an arithmetic device for constructing the 3-dimensional image by carrying out au arithmetical operation for the refraction angle data from the imaging device.

13 Claims, 13 Drawing Sheets

3-DIMENSIONAL IMAGE CONSTRUCTION METHOD AND APPARATUS

TECHNICAL FIELD

The present invention relates to a 3-dimensional image construction method and apparatus, particularly to a 3-dimensional image construction method and apparatus using a refraction contrast.

BACKGROUND ART

An X-ray CT (computed tomography) of the inner structure of an object is a very powerful tool for the nondestructive observation. Since the development in early 1970's, it has found numerous applications in many fields of science, technology and medicine. Most of the methods which utilize the principal scheme of the CT are based on an X-ray absorption contrast. For example, a 3-dimensional medical image based on an X-ray absorption contrast considerably contributes to a medical diagnosing in addition to an ultrasonic image and an MRI (magnetic resonance imaging) in a medical field.

However, in recent years, X-ray imaging techniques have rapidly been developing and utilized a new kind of contrasts. One of the contrasts is a refraction contrast (i.e., the distribution of the X-ray intensity dependent on the refraction of the X-ray penetrated through an object).

In general, the refraction contrast may be any kind of the X-ray images with the intensity distribution thereof being a function of a refraction angle. Main advantages of the refraction contrast are the possibility to observe tiny cracks and deformations invisible in other types of contrasts and better sensitivity to the low Z materials. This is of great importance in medical imaging. The CT-reconstruction based on the refraction contrast has been expected to possess the same advantages.

DISCLOSURE OF THE INVENTION

Problems to be Solved

The inventors of the present application have studied the contrast diagnosing for a coronary artery by injecting a contrast medium into a vein since 1997, and have recognized that there are many internal organs which are invisible or have problems in image quality by the ordinary absorption contrast. The inventors have intended to make these internal organs visible, become there have been a possibility such that a visible 3-dimensional image of the internal organs invisible by the conventional absorption contrast method may be constructed.

A CT-reconstruction by the refraction contrast has been attempted until now, but the reliable image of an object has not been realized.

The object of the present invention is to provide a method and apparatus for constructing a 3-dimensional image of the internal organs invisible by the conventional method.

Means for Solving the Problems

The X-ray CT-reconstruction technique has been widely used in many fields of research. In general, the CT-reconstruction is based on the absorption contrast described above. Recently, the methods for generating another contrasts have been developed. One of the contrasts is the refraction one due to the change of propagating direction of the X-ray beam when the parallel X-ray beam penetrates through an object. The refraction contrast has advantages such that portions invisible by the absorption contrast may be observe. Therefore, the CT-reconstruction method based on the refraction contrast has also the same advantages described above. However, this method requires a new mathematical algorithm and software.

The present invention solved the problems including establishment of a theoretical formula for a mathematical model which is the base for a computer modeling and experimental realization of technique.

A first aspect of the present invent is an apparatus for constructing a 3-dimensional image of an object. The apparatus comprises:

generating means for generating a monochromatic and parallel X-ray beam from an X-ray beam;

an angle analyzer for reflecting or transmitting the monochromatic and parallel X-ray beam passing through the object positioned on a rotatable goniometer in the monochromatic and parallel X-ray beam;

an imaging device for generating a refraction angle data by receiving the monochromatic and parallel X-ray beam reflected on or transmitted through the angle analyzer to defect the intensity thereof and output a refraction angle data; and an arithmetic device for constructing the 3-dimensional image by carrying out an arithmetical operation for the refraction angle data from the imaging device; wherein the arithmetic device extracts, from the refraction angle data, a refraction angle distribution $\Delta\alpha(\Theta_r,t)$, herein $\Theta$ is a rotation angle of the object and t is a projection coordinate perpendicular to the X-ray beam, and reconstructs a refraction index gradient $\nabla\tilde{n}$ from the extracted refraction angle distribution $\Delta\alpha(\Theta_r,t)$, and the reconstruction of the refraction index gradient $\nabla\tilde{n}$ is carried out by an algorithm $$\Delta\alpha(\Theta,t)e^{i\Theta} = \int_S |\nabla\tilde{n}(r)| e^{i\phi(r)} dr$$

herein $\tilde{n}(r)$ is a local refraction index which has a relation to the refraction index n(r) in portion r as $\tilde{n}=1-n$, $\phi(r)$ is the angle between the direction of the X-ray beam and the refraction index gradient $\nabla\tilde{n}(r)$, and S is an integration path.

A second aspect of the present invention is a method for constructing a 3-dimensional image of an object. The method comprises the steps of:

generating a monochromatic and parallel X-ray beam from an X-ray beam by a monochromator-collimator;

reflecting or transmitting the monochromatic and parallel X-ray beam passed through the object positioned on a rotatable goniometer in the monochromatic and parallel X-ray beam, and receiving the monochromatic and parallel X-ray beam reflected on or transmitted through the angle analyzer by an imaging device to acquire a refraction angle data; and constructing the 3-dimensional image by carrying out an arithmetical operation for the refraction angle data from the imaging device; wherein the arithmetical operation includes the steps of, extracting a refraction angle distribution $\Delta\alpha(\Theta_r,t)$, herein $\Theta$ is a rotation angle of the object and t is a projection coordinate perpendicular to the X-ray beam, reconstructing a refraction index gradient ∇ñ from the diffraction angle distribution Δα(Θ,,t), and converting the reconstructed refraction index gradient ∇ñ to a scalar field ñ (r).

ADVANTAGEOUS EFFECTS OF THE INVENTION

In accordance with the present invention, the problems for a mathematically correct algorithm of the CT-reconstruction based on the X-ray refraction contrast has been solved. The software prepared by this algorithm has showed good results.

Also, the 3-dimensional image construction method and apparatus have following advantageous effects;
(1) A cartilage may be imaged, and
(2) Breast cancer cell, connective tissue, stroma, milk duct (ductus lactiferi), blood vessel, collagenous fiber of stroma, and the like may be imaged.

BEST MODE FOR CARRYING OUT THE INVENTION

A refraction contrast is based on the distribution of an X-ray intensity due to the refraction of an X-ray beam which penetrates through an object. In most cases, the refraction contrast is mixed with an absorption cons Fortunately, by the current technique, the information on a refraction angle distribution can be extracted from the mixture of the refraction and absorption contrasts. The refraction angle Δα of the X-ray beam penetrating through an object is calculated as the integral over the x-ray beam path S with the elemental refraction as the integrand:

$$\Delta\alpha = \int_S |\nabla \tilde{n}(r)| \sin \phi(r) dr \quad (1)$$

where ñ (r) is a local refraction index which has a relation to the refraction index n(r) in position r as ñ=1−n, φ (r) is the angle between the X-ray beam direction and the refraction index gradient ∇ñ (r), i.e., the angle between the X-ray beam direction and the differentiation of the local refraction index ñ.

In this integral, the X-ray beam path S inside the object may be approximated by a straight line taking into account the fact that ñ≦$10^{-5}$ in the X-ray region.

The equation (1) is not enough for the CT-reconstruction, because it has two unknown functions: the absolute value of the refraction index gradient |∇ñ| and the angle φ (r) both of which may not be obtained independently.

Since the values of the refraction index ñ are equal on both sides of the object, the difference between them has always zero value:

$$0 = \int_S |\nabla \tilde{n}(r)| \cos \phi(r) dr \quad (2)$$

Equations (1) and (2) may be written in the complex form, if the equation (2) is multiplied with complex unity i and is added to the equation (1)

$$\Delta\alpha = -i \int_S |\nabla \tilde{n}(r)| e^{i\phi(r)} dr \quad (3)$$

Figure 1:
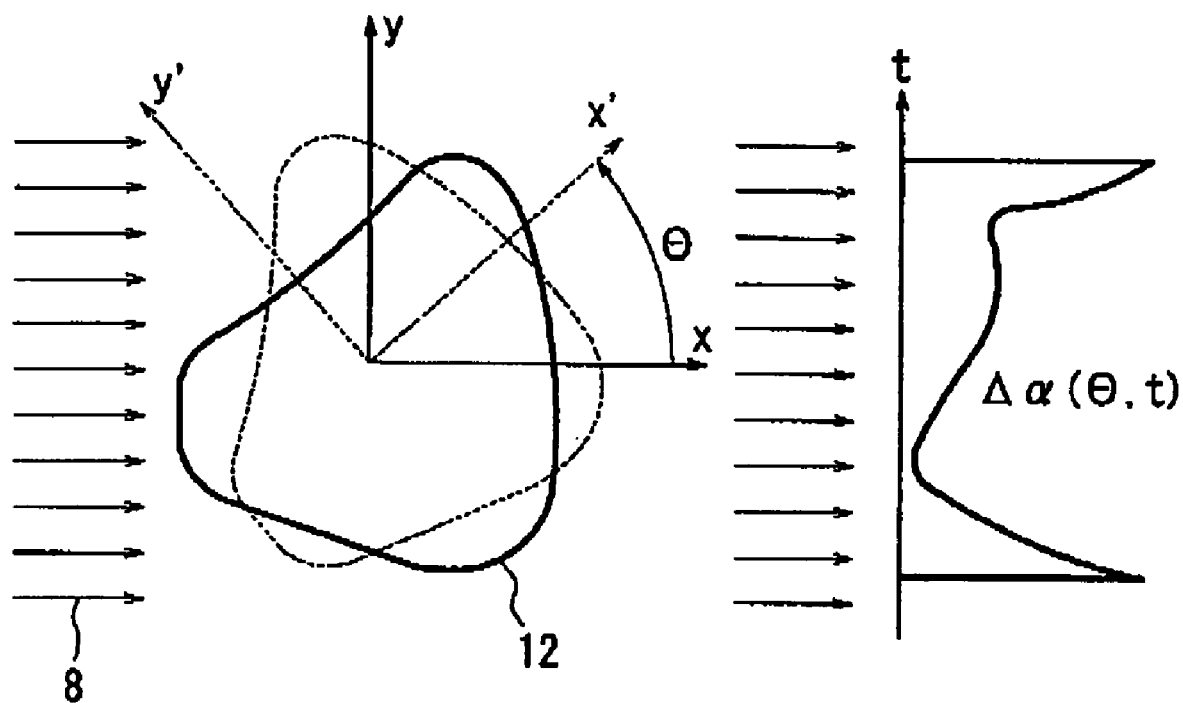
FIG. 1 is a view showing the basic CT geometry.

This equation serves as the base for the CT-reconstruction equation. FIG. 1 shows a basic CT geometry. An object 12 is positioned on a rotatable goniometer in an X-ray beam 8. Herein, Θ is the angle between the initial position and present position (designated by a dotted line, t is the projection coordinate perpendicular to the X-ray beam 8, and a refraction angle distribution Δα(Θ,,t) is the projection with the information about the refraction angle.

According to the general CT method, it is needed to acquire the information on the refraction angle as the information on the angular position of the object Θ and the space coordinate t. Therefore, after mathematical manipulations with the equation (3), the algorithm for the CT-reconstruction may be written as follows:

$$\Delta\alpha(\Theta,t) e^{i\Theta} = \int_S |\nabla \tilde{n}(r)| e^{i\phi(r)} dr \quad (4)$$

with the integration path S being the straight line
x cos Θ+y sin Θ=t.

The equation (4) denotes that the result of the CT-reconstruction is the gradient of the field of refraction index. One can note that the equation (4) is very similar to the equation for the absorption contrast based CT-reconstruction. The difference is in the input fractions (they are Δα(Θ,,t) exp (iΘ) for the refraction contrast and log(Θ,,t)/$I_0$) for the absorption contrast, and in the functions to be reconstructed (they are |∇ñ (r)|expiφ (r) for the refraction contrast and μ(r) for the absorption contrast).

However, there is one important difference between theses cases of refraction contrast and absorption contrast. In the equation for the absorption contrast based CT-reconstruction, both input and output functions are in the real number space, while the refraction contrast based CT-reconstruction utilizes the functions in the complex number space. This means that the absorption contrast based CT algorithm may not be adopted for the case of the refraction contrast and its own original algorithm and software are required.

Due to the structure of the equation (4), the mathematical formalism of the refraction contrast based CT algorithm is the same as that is used for the case of absorption contrast (so called Filtered Backprojection method). Basically, the mathematical formalism consists of the following four steps.

i) Fourier transform of the input function $\Delta\alpha(\Theta,t)$ exp i $\Theta$(which is often called "sinogram"):

$$P_\Theta(\omega) = \int_{-\infty}^{\infty} \Delta\alpha(\Theta,t) \exp i\Theta e^{-2\pi i\omega t} dt. \quad (5)$$

ii) Filtering of the transformed function $P_\Theta(\omega)$:

$$S_\Theta(\omega) = P_\Theta(\omega) b(\omega) \quad (6)$$

Herein, $b(\omega)$ is a filtering function. There are a lot of filtering functions used in the CT-reconstruction. However, the filtering functions usually used in the absorption abstract based CT-reconstruction are hardly applicable in the refraction contrast, because all of the filtering functions suppress high frequency components emphasizing low frequency ones. It is reasonable in case of absorption contrast, because most useful information is contained in the low domain, while high frequency components mostly consists of noise. Contrastingly, in case of refraction contrast, higher Fourier components play important role and should not be suppressed by the filtering function.

iii) Backward Fourier transform of the filtered function:

$$Q_\Theta(t) = \int_{-\infty}^{\infty} S_\Theta(\omega) |\omega| e^{2\pi i\omega t} d\omega. \quad (7)$$

The resulting function $Q_\Theta(t)$ is known as the filtered sinogram.

iv) Backprojecting of the filtered sinogram to the real space.

$$|\nabla \tilde{n}(x) = \exp i\phi(r) = \int_0^\pi Q_\Theta(t) d\Theta \quad (8)$$

Herein, $r \equiv (x, y)$ corresponds to t as $t = x \cos\Theta + y \sin\Theta$. This algorithm is presented for the continuous form of the equations. However, in any practical application, the function $\Delta\alpha(\Theta,t)$ is known only in a certain points $\Theta_m$ and $t_n$. Therefore, the discrete form of the algorithm must be used in actual calculations.

The refraction contrast based CT equation (4) shows that the reconstructed function is the gradient of the refraction index $\Delta\tilde{n}(r)$, while most users would prefer the results in the form of the real physical values $\tilde{n}(r)$ rather than its gradients. In order to calculate the real physical values, the CT-reconstruction is first performed, and then the scalar field $\tilde{n}(r)$ is built from the gradient $\nabla\tilde{n}(r)$ using the property of the scalar field gradient $$\tilde{n}(r_0) = \int_\infty^{r_0} \nabla \tilde{n}(r) dr. \quad (9)$$

However, the basic equality $\nabla \times (\nabla \tilde{n}(r)) \equiv 0$ is not fulfilled strictly due to the arithmetical error in step (iv) of the CT-reconstruction algorithm (see the equation (8)). This means that the value of the scalar field $\tilde{n}(r_0)$ depends on the choice of the integration path so that it is needed to calculate two or more integral equations (9) along the different trajectories and then use that average thereof as the most realistic result. In order to avoid this problem, another way is used to reconstruct the value $\tilde{n}$. The gradient-to-field conversion may be done before the backprojecting of the filtered projection equation (8), since the physical meaning of the filtered sinogram $Q\Theta(t)$ is the projection of the gradient $\nabla\tilde{n}(r)$. Then, in the fourth step (iv) of the reconstruction algorithm, the new function $$Q_\Theta^{integrated}(t) = \int_\infty^t Q_\Theta(r) dr \quad (10)$$

is used instead of the function $Q_\Theta(t)$. After this transformation, the reconstructed function is the equation (8) is not the gradient, but the refraction index itself. The gradient-to-field conversion built in inside the reconstruction algorithm has certain advantages over the conversion performed after the reconstruction. First of all, the integral equation (10) is one-dimensional contrastingly to the integral equation (9) which is performed over a curve on the surface (x,y). This makes the integration mathematically easier and computationally cheaper. Secondary, the equality $\nabla \times (\nabla \tilde{n}(r)) \equiv 0$ holds true strictly before the fourth step of the algorithm due to the member $|\omega|$ in the integrand of the equation (7) which grantees the mean value of the function $Q_\Theta(t)$ equal to zero.

Embodiment 1

An embodiment of the 3-dimensional image construction method and apparatus in accordance with the present invention will now be described. The problem of the experimental derivation of the function $\Delta\alpha(\Theta,t)$ is the equation (4) is not obvious and different techniques have been proposed until now. The most reliable one of them is the diffraction enhanced imaging (DEI) method presented in 1997.

Figure 2:
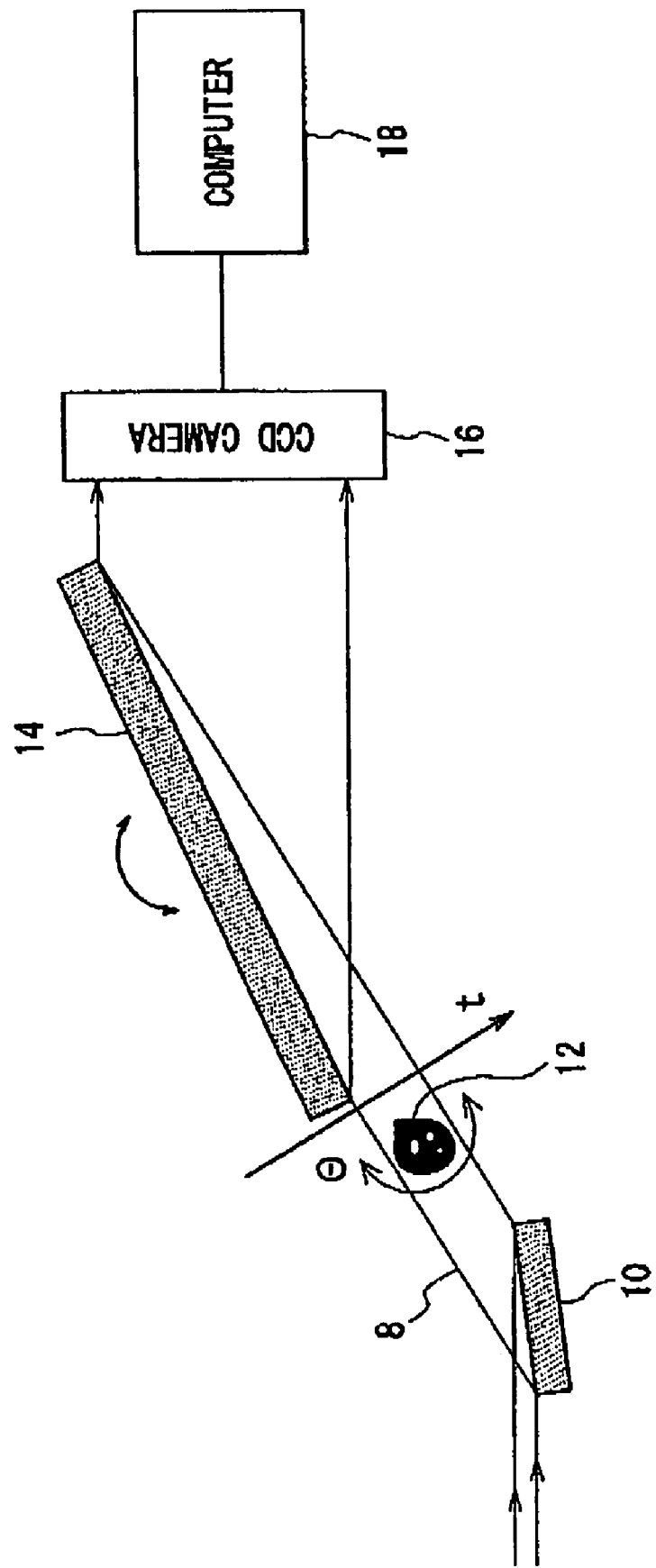
FIG. 2 is a schematic view of one embodiment of the 3 dimensional image construction apparatus in accordance with the present invention.

The schematics of the experiment performed in accordance with the DEI method is presented in FIG. 2. Reference numeral 10 designates an asymmetrical monochromator which makes the X-ray from the X-ray source (not shown in the figure) to a monochromatic parallel beam (plane wave), and reference numeral 12 an object (or sample) under investigation. The rotation axis for the CT scanning over the angle $\Theta$ is perpendicular to the image plane. Reference numeral 14 designates a reflection-type angle analyzer, and 16 a CCD (solid imaging device) camera. The diffraction angle data from the CCD camera 16 is transferred to a computer 18 which is an arithmetic device.

Photon energy used in the embodiment was 11.7 keV. Both the monochromator 10 and angle analyzer 14 used Si(220) which was diffraction type and was asymmetrically cut with 9.5°. At these conditions, Bragg angle $\Theta_B = 16.0°$ and a asymmetry factor b=3.8. The CCD camera used had a view area of 10.0 mm (width)×7.5 mm (height) with 1384×1032 pixels. The horizontal and vertical dimensions of view area are different due to the asymmetrical reflection.

The choice of the asymmetrically cut crystals was done reasoning from the size of the object, the view area of the CCD camera, and the width of reflective curve, i.e., rocking curve of the angle analyzer 14. However, the monochromator 10 and angle analyzer 14 are not limited to a asymmetrically cut Si crystal.

The present embodiments was performed at the vertical wiggler beamline BL14B at a synchrotron radiation facility (Photon Factory) of High Energy Accelerator Research Organization.

The X-ray beam (lane wave) 8 reflected from the asymmetrical monochromator 10 passes through the object 12, and is incident on the angle analyzer 14 to be analyzed in angle. At this time, two reflecting positions of the angle analyzer 14, i.e., the positions on the left and right slopes from the reflecting peak of the rocking curve are selected.

The X-ray beam reflected on the angle analyzer 14 is acquired by the CCD camera 16 to generate the refraction contrast.

Figure 3:
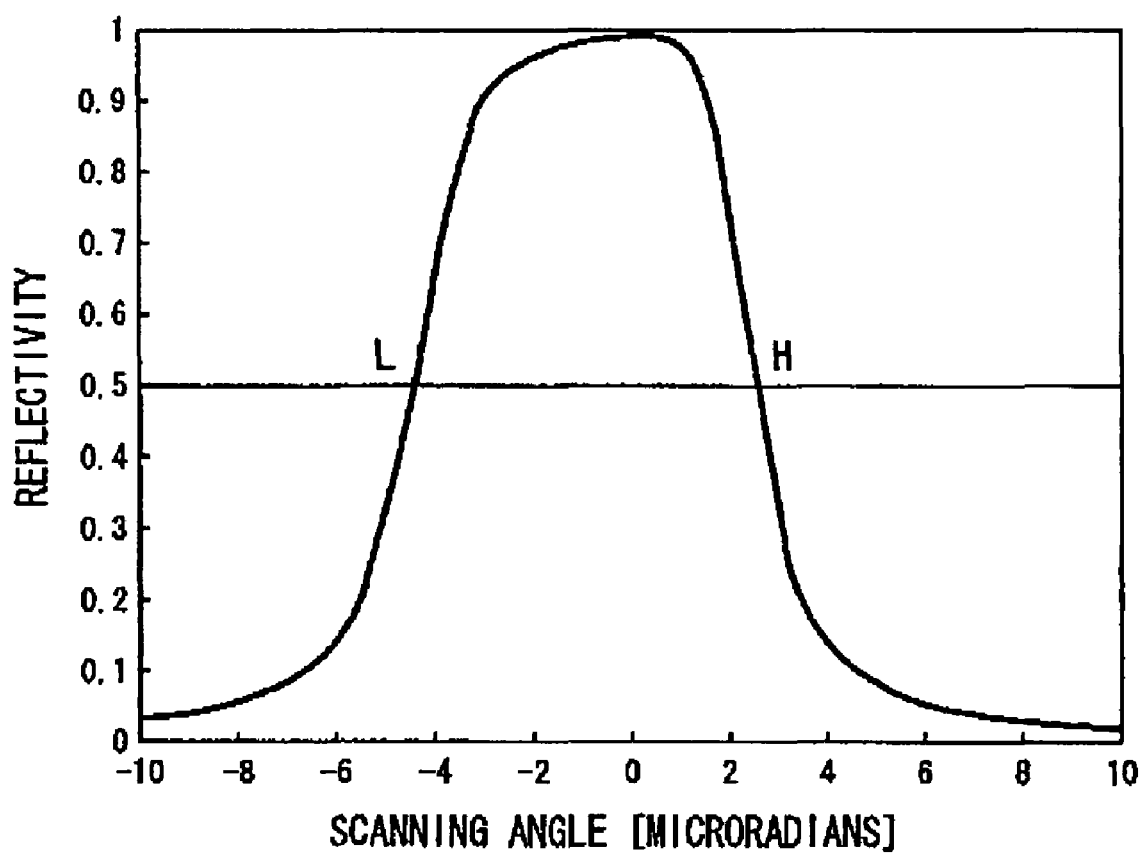
FIG. 3 is a view showing the racking curve of the analyzer

The rocking curve of the angle analyzer 14 is shown in FIG. 3. In order to extract the refraction angle data in accordance with the DEI method, it is required that two pictures of the same object at two positions of the analyzer 14 are taken. In FIG. 3, these two positions of the analyzer 14 (reflecting points where angle information may be extracted to a maximum extent from the contrasts) are denoted as positions L and H. The position L is on the left slope from the reflecting peak of the rocking curve, and the position L on the right slope. In the figure, each of the positions L and H designates the height of half-width. The positions L and H may be varied in their height on condition that they have the same height.

Series of images for reconstruction are taken in the points L and H of the rocking curve. The reflectivity in both L and H points is 0.5.

The refraction angle may be calculated according to the equation (6b) disclosed in the reference "D. Chapman, W. Thomlinson, R. E. Johnston, D. Washburn, E. Pisano, N. Gmür, Z. Zhong, R. Menk, F. Arfelli and D. Sayers, Phys. Med. Biol. 42, 2015 (1997)". However, the theoretical model used in the above reference utilizes the Taylor expansion of the rocking curve and therefore it is suitable only in limited ranges. In order to increase the degree of accuracy, the rocking curve of the analyzing crystal is utilized instead of its Taylor approximation. The result of the refraction angle extraction is shown in is FIGS. 4A, 4B and 4C.

The sample presented in these figures is a fragment of the refill for the ball point pen deformed by fire. This sample was chosen because (i) it has no central symmetry, (ii) absorption contrast is low at 11.7 keV, and (iii) it consists of different substances (plastic body with ink and air spaces inside).

A method for constructing a 3-dimensional image by utilizing the sample will now be described in every step.

(1) The monochromator 10 and angle analyzer 14 are positioned as shown in FIG. 2. The angle analyzer 14 is rotated to obtain a reflection curve (rocking curve).
(2) The reflection position is adjusted to the point L of the rocking curve.
(3) The sample 12 is set.
(4) The transmitted X-ray and refracted X-ray through the sample 12 are reflected on the angle analyzer 14 and are incident on the CCD camera 16. The refraction angle data from the CCD camera 16 is input into the computer 18.
(5) The sample 12 is removed.
(6) In the condition of no sample 12, a plane wave is reflected on the angle analyzer 14 and is input into the CCD camera 16. The refracted angle data is input into the computer 18.
(7) In the computer 18, the refracted angle data acquired in the step 6 is subtracted from the refracted angle data acquired in the step 4.
(8) The sample 12 is set again and the sample is rotated to a subsequent angle.
(9) The operations in the step 4-7 are repeated.
(10) The same operations are continued until the rotating angle of the sample is reached 180°.
(11) The reflection position is adjusted to the point H of the rocking curve.
(12) The operations in the steps 3-10 are repeated.
(13) The refraction angle is extracted by computing two kinds of data acquired in step 7 for two reflecting positions of the angle analyzer.
(14) The image is extracted due to the Filtered Backprojection method by utilizing the equation (4).

Figure 4A:
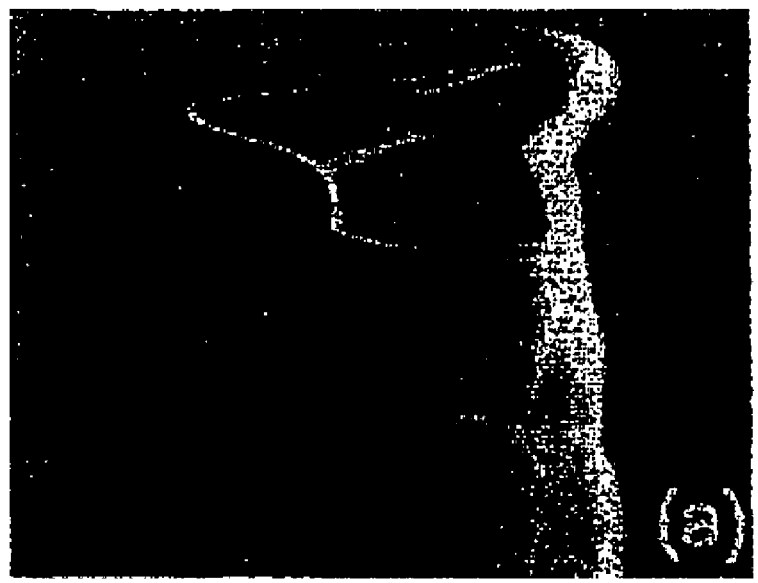
FIG. 4A is a photograph showing the sample image taken at the position L of the rocking curve of the analyzer.
Figure 4B:
FIG. 4B is a photograph showing the sample image taken at the position H of the rocking curve of the analyzer.

FIGS. 4A and 4B show the original images in L and H positions of the rocking curve of the angle analyzer 14, respectively. In these images, noises are subtracted, i.e., the background image without the sample is subtracted from the image with sample. FIG. 14C shows the extracted refraction angle $\Delta\alpha$ proportional to the intensity of the gray scale with zero deflection corresponding to the middle gray.

According to the above described description, the refraction contrast based reconstruction process consists of the following steps:

(i) Taking set of images at different $\Theta_{,m}=m\Delta\Theta$ (with m an integer varying in ranges from 0 to M and $\Delta\Theta=180°/M$) in the L point of the rocking curve (see FIG. 4A).

(ii) Taking set of images at different $\Theta_{,m}=m\Delta\Theta$ (with m an integer varying in ranges from 0 to M and $\Delta\Theta=180°/M$) in the H point of the rocking curve (see FIG. 4B).
(iii) Extracting $\Delta\alpha(\Theta m, t)$ from the sets of images according to the modified DEI method (see FIG. 4C for the extracted data).
(iv) CT-reconstruction of a slice on the basis of Equation (4). As a result of T-reconstruction, the gradient $\Delta\tilde{n}$ is obtained.
(v) Transformation of the gradient $\Delta\tilde{n}$ to the more suitable local refraction index.

The number of projections of the object in the embodiment was M=360 which gives $\Delta\Theta=0.5°$.

Figure 4C:
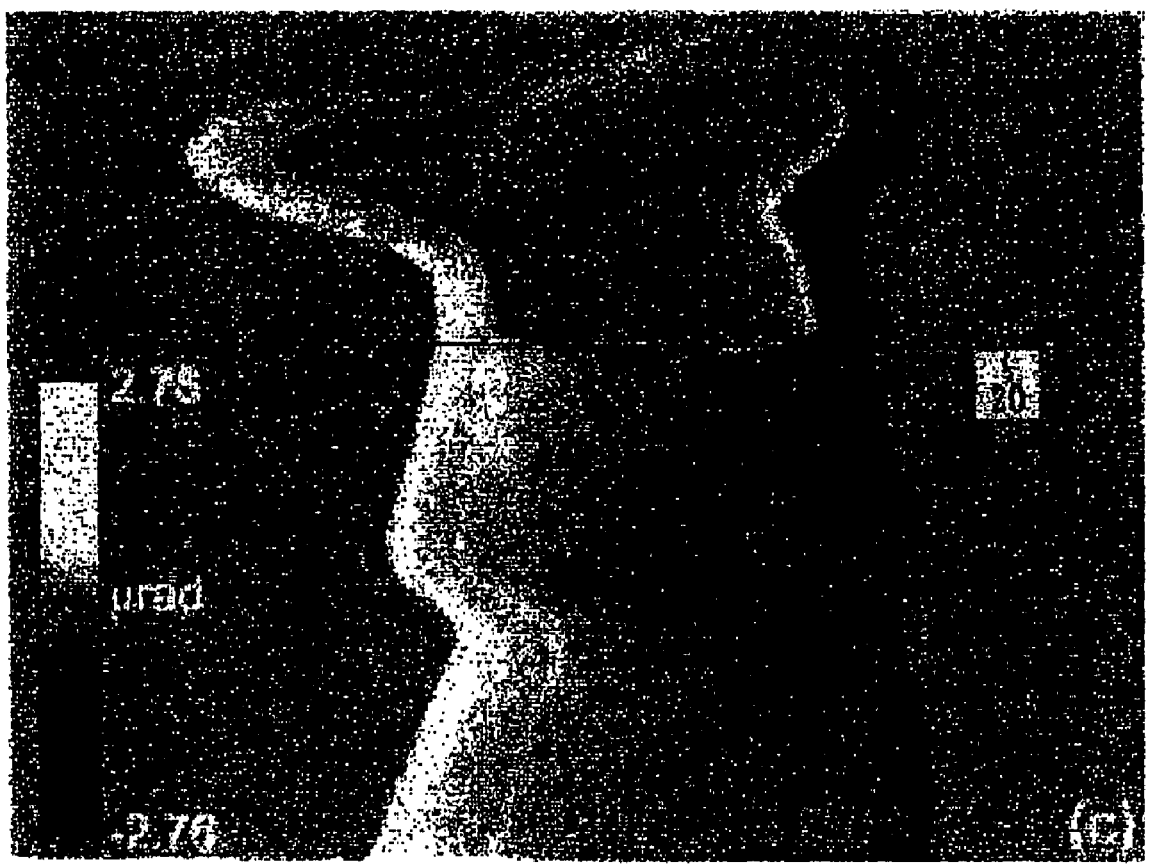
FIG. 4C is a photograph showing the diffraction angle distribution Δα extracted from the images in FIGS. 4A and 4B.
Figure 5A:
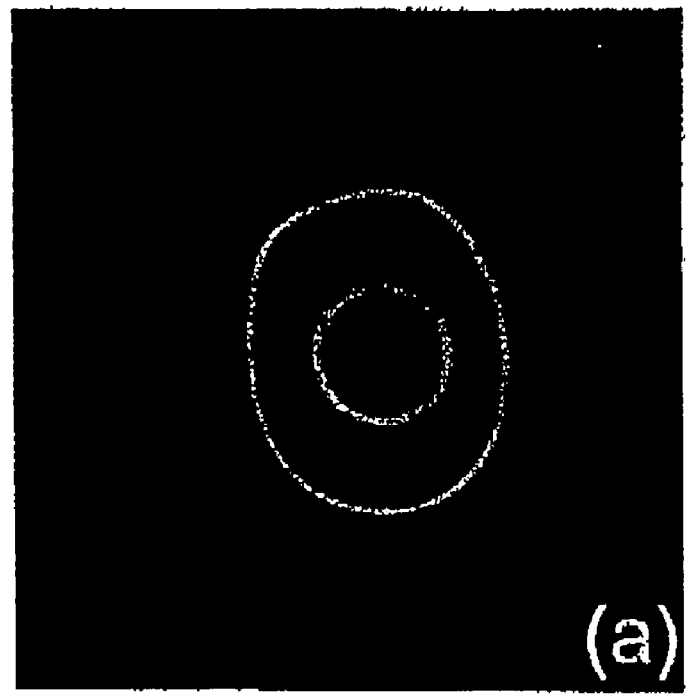
FIG. 5A is a photograph showing the reconstructed image.
Figure 5B:
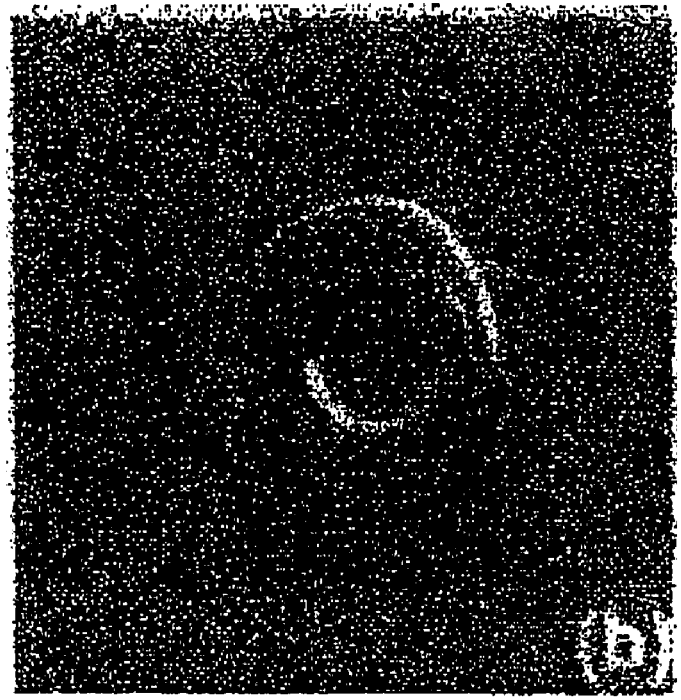
FIG. 5B is a photograph showing the reconstructed image.
Figure 5C:
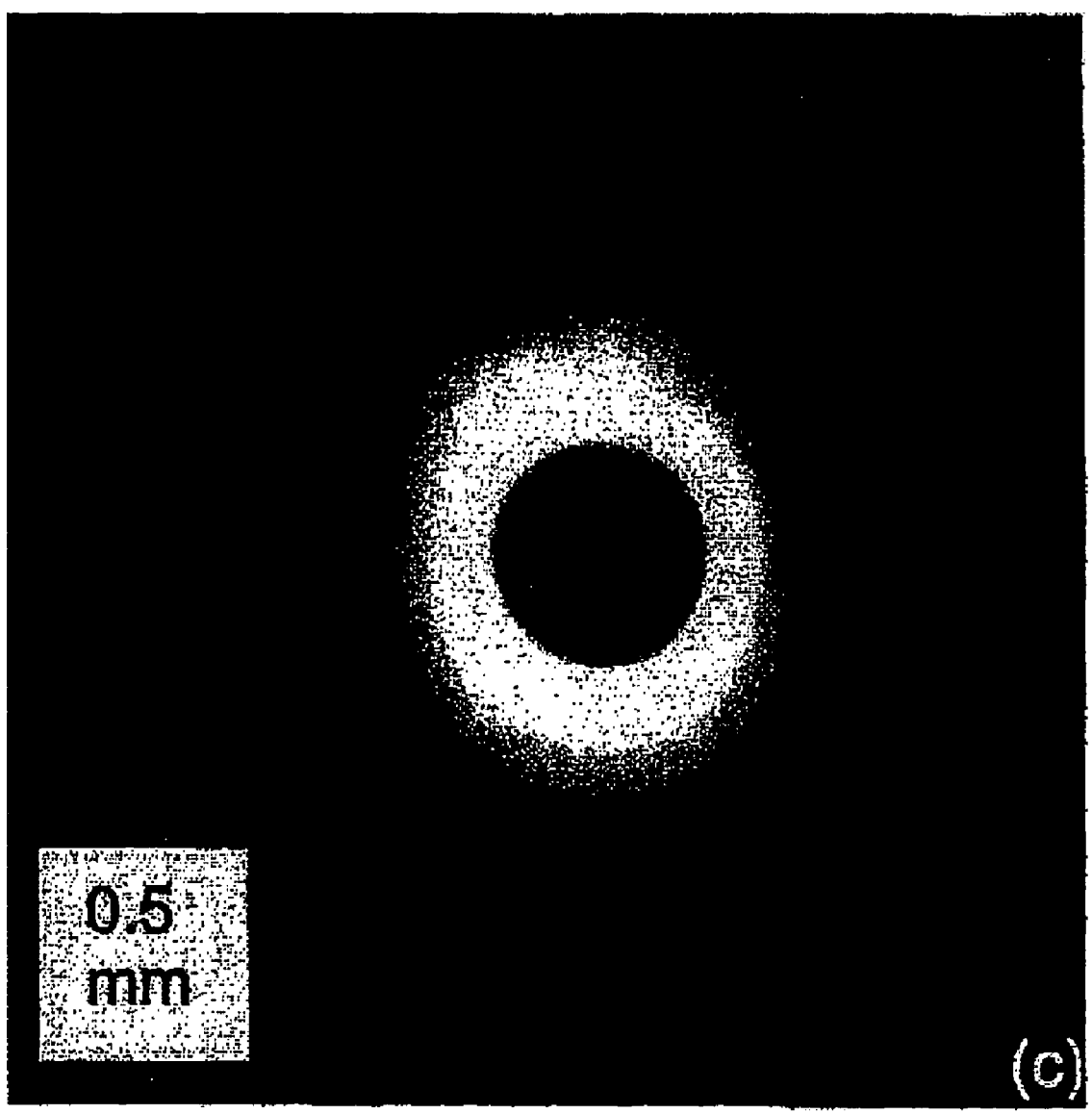
FIG. 5C is a photograph showing the reconstructed image of the slice designated by the dotted line in FIG. 3.

The reconstructed two-dimensional image of the slice marked in FIG. 4C with the dotted line are shown in FIGS. 5A, 5B and 5C. FIG. 5A shows the reconstruction $\Delta\tilde{n}$ in the form of $|\nabla\tilde{n}|$ for the slice (a 2-dimensional slice image), FIG. 5B the reconstruction $\Delta\tilde{n}$ is the form of $|\nabla\tilde{n}\sin\phi|$ for the slice (a 2-dimensional slice image), and FIG. 5C the result of $|\nabla\tilde{n}|\rightarrow|\tilde{n}|$ transformation (a 2-dimensional slice image).

It is noted that the object on the reconstructed imaged has fuzzy edge. This is the consequence of the X-ray optics limitations which appears mainly due to the Borrmann fin effect, the source size, and the propagation-interference contrast. It is expected that the edge fuzziness can be partially suppressed with the decrease of the object-to-detector distance (it was 138 cm in the embodiment).

The 2-dimensional slice image shown in FIG. 5C proves to be very interesting, because it shows all three materials (plastic body, ink, air inside). All three materials are distinguishable in contrast. The refraction index of the ink proved to be larger than that of the plastic body. This is because black ink is made using carbon black and has inclusions of pigments such as titanium dioxide.

Figure 6:
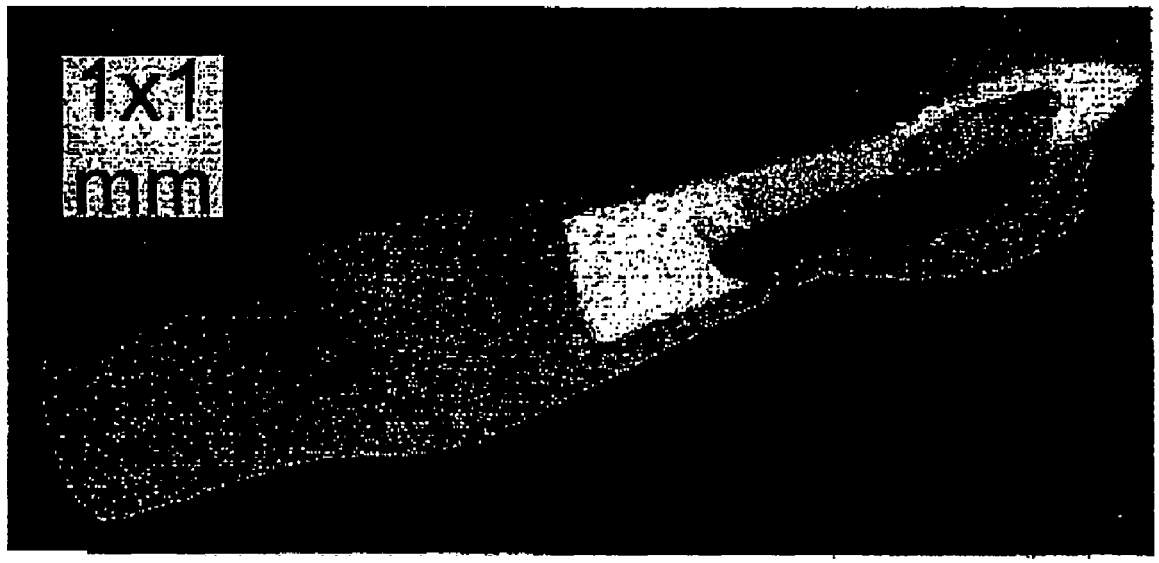
FIG. 6 is a photograph showing the 3-dimensional representation of the object.

A 3-dimensional image is acquired by constructing all of the reconstructed 2-dimensional slice images. The 3-dimensional representation of the object is displayed in FIG. 6. They are realistic representation of the sample.

One more artifact comes from $\nabla\tilde{n}\rightarrow\tilde{n}$ transformation and can be recognized as a netlike contrast of pixel size in FIG. 5C. It is possible to erase this unwanted contrast but it takes one order longer computation time and for most cases may be left as is since it does not distort the image strongly.

Figure 7A:
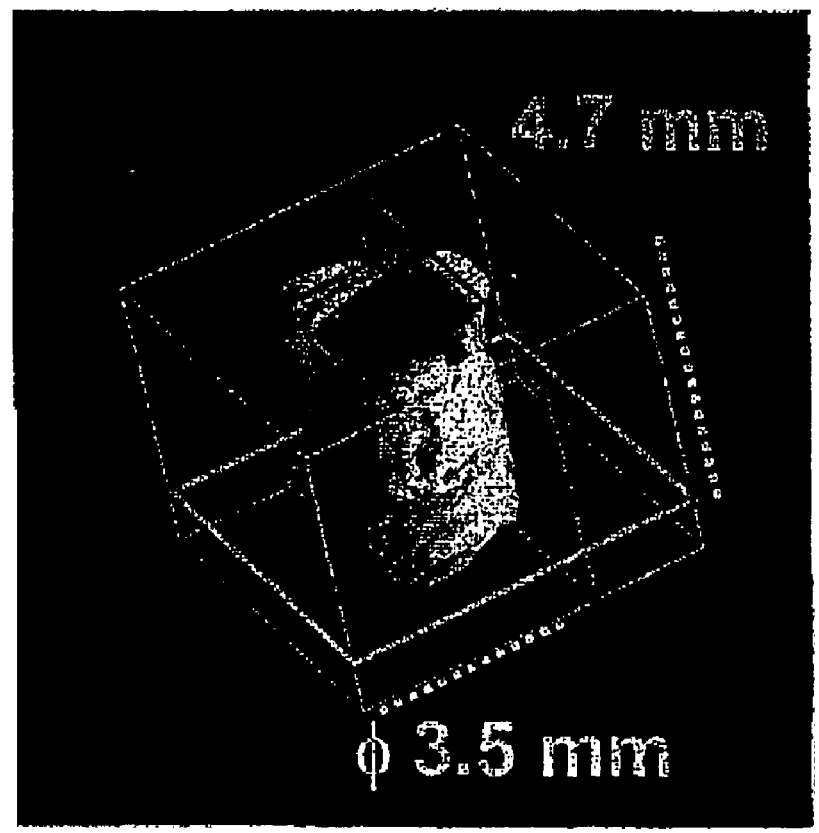
FIG. 7A is a photograph showing an example of the 3-dimensional image for sample piece of invasive micropapillary carcinoma
Figure 7B:
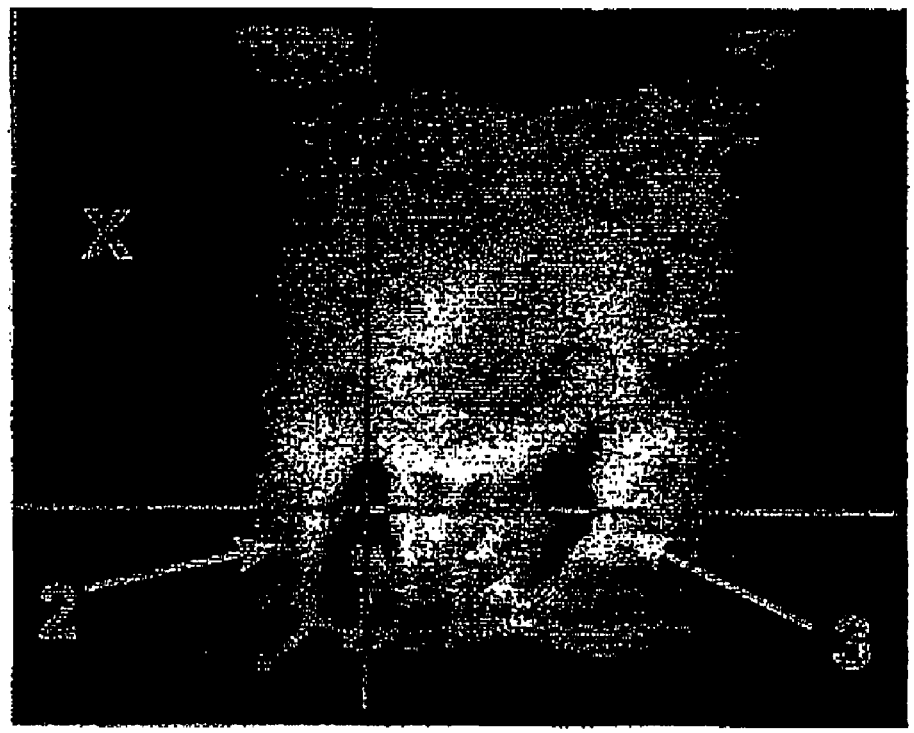
FIG. 7B is a photograph showing the 2-dimensional slice image in the 3-dimensional image shown in FIG. 7A.
Figure 7C:
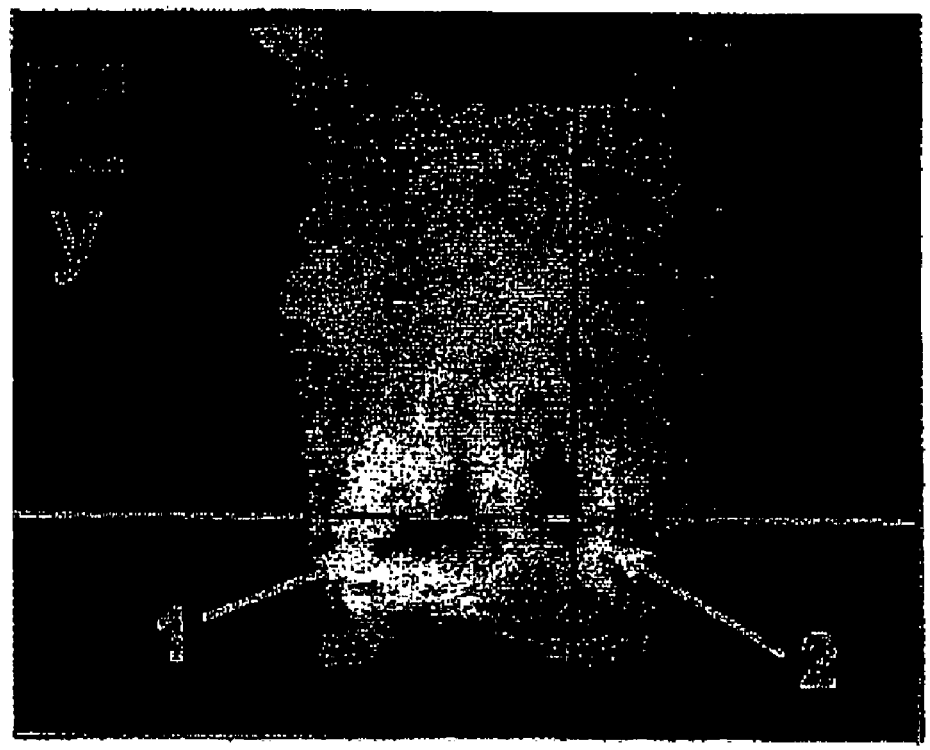
FIG. 7C is a photograph showing the 2-dimensional slice image in the 3-dimensional image shown in FIG. 7A.
Figure 7D:
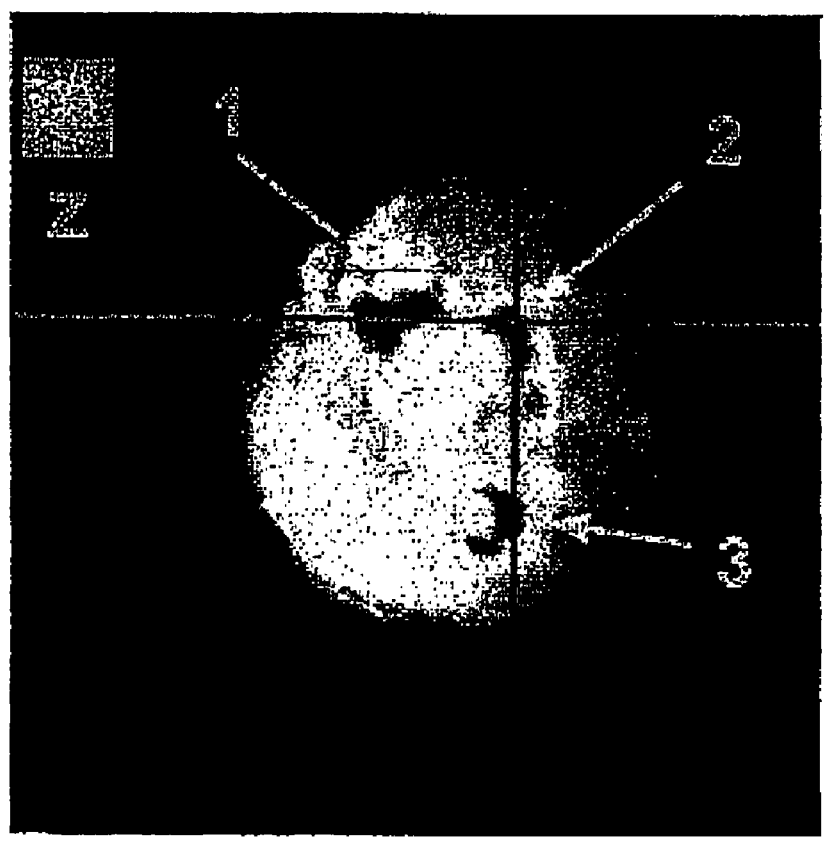
FIG. 7D is a photograph showing the 2-dimensional slice image in the 3-dimensional image shown in FIG. 7A.

FIG. 7A shows an example of the 3 dimensional image for sample piece of micropapillary carcinoma. The 2-dimensional slice images of the 3-dimensional image are shown in FIGS. 7B, 7C and 7D, respectively. FIG. 7B shows the 2-dimensional slice image in an X-plane, FIG. 7C the 2 dimensional slice image in a Y-plane, and FIG. 7D the 2-dimensional slice image in a Z-plane, respectively.

These 2-dimensional slice images show three milk ducts designated by numerals 1, 2 and 3. A high contrast area is observed in the center of the breast duct. The high contrast area is recognized as calcification. A low contrast area is observed in proximity to the calcified area. The low contrast area is recognized as a necrotic area A higher contrast area surrounds the low contrast necrotic area. The higher contrast area is recognized as a cancer cell tissue. A high contrast linear area or net area is observed outside the breast duct. This area is recognized as an invasive cancer cell tissue. In particular, the breast duct 3 observed in FIG. 7D is substantially occluded. Furthermore, it is easily recognized that almost of breast ducts have a white edge surrounding the breast duct, respectively. The white edge region denotes a higher density of electrons. Even irregular shape of spreading invasive malignant tumor may be observed clearly.

Figure 8:
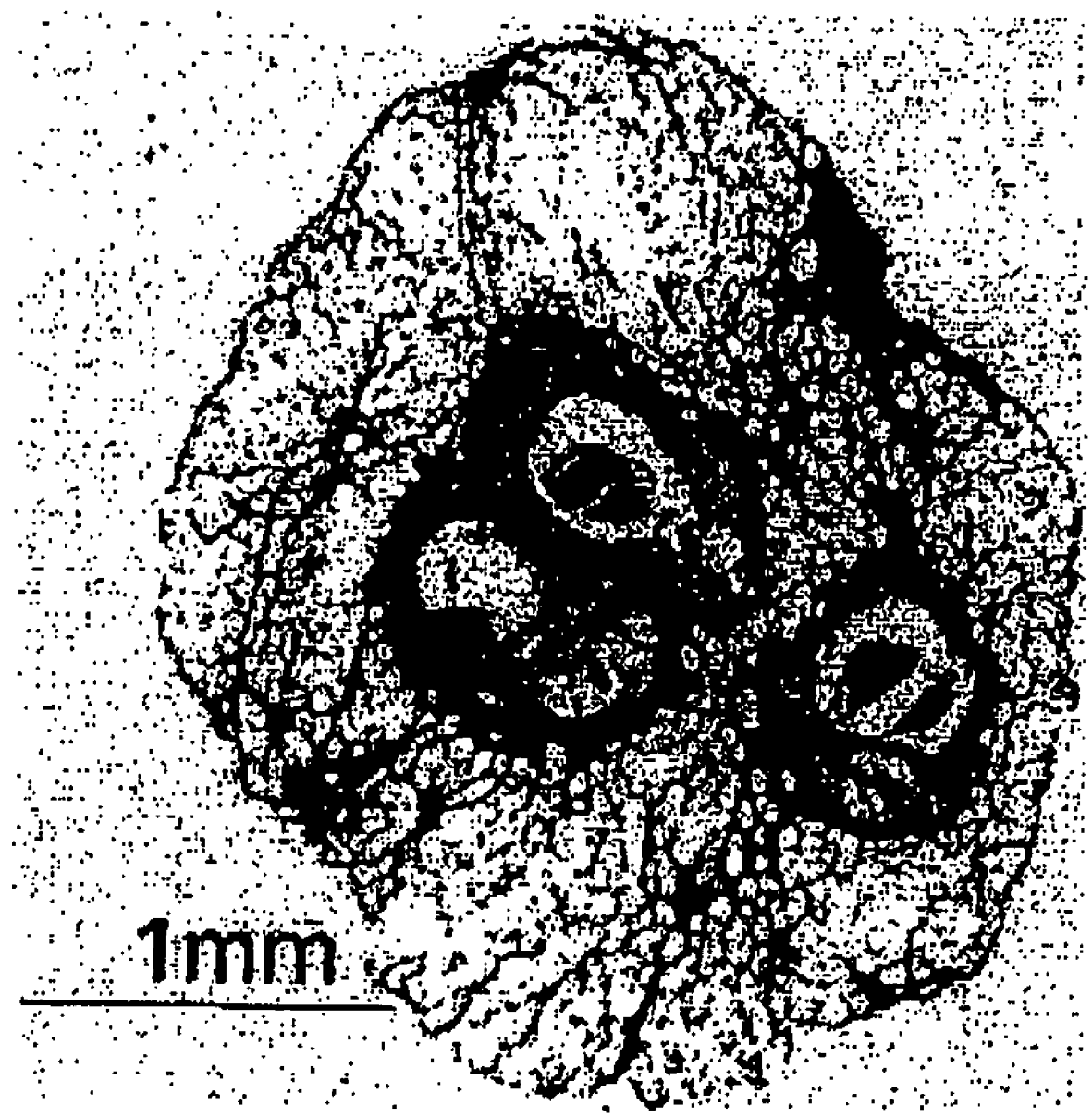
FIG. 8 is a dyed pathological view corresponding to the 2-dimensional slice image in the 3-dimensional image shown in FIG. 7D.

FIG. 8 shows a dyed pathological view corresponding to the 2-dimensional slice image in FIG. 7D. This dyed pathological view has extremely good correspondence to the 2-dimensional slice image formed by the 3-dimensional image construction apparatus in accordance with the present invention, so that there is a possibility such that the refraction contrast based CT image according to the present invention may be replaced by the dyed pathological view.

In order to find out a breast cancer as early as possible, a mammography is particularly useful. The current mammography uses the X-ray absorption contrast. The best space resolution in the current mammography based on the X-ray absorption contrast is at most 50 µm, while the 3-dimensional image construction apparatus based on a refraction contrast according to the present invention has realized a space resolution in the range of 5-10 µm. Thereby, an X-ray pathological diagnosis would be developed.

Embodiment 2

Figure 9:
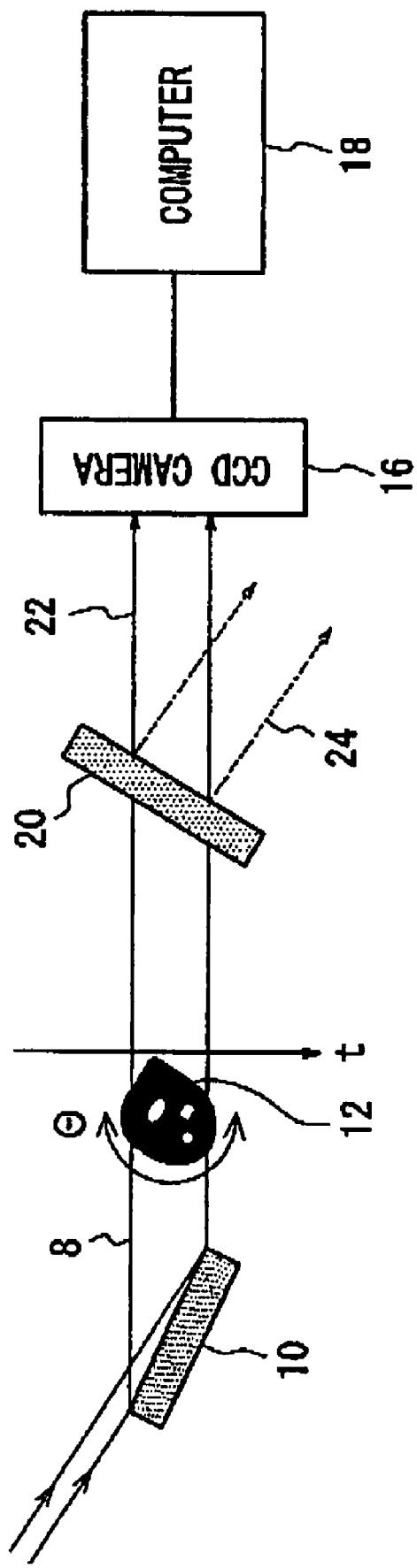
FIG. 9 is a schematic view of another embodiment of the 3-dimensional image construction apparatus in accordance with the present invention.

While the reflection-type angle analyzer is used in the embodiment 1, a transmission-type angle analyzer may be used. FIG. 9 shows a 3-dimensional image construction apparatus using a transmission type angle analyzer 20. In the figure, the same components as that in FIG. 2 are designated by the same reference numerals.

Figure 10:
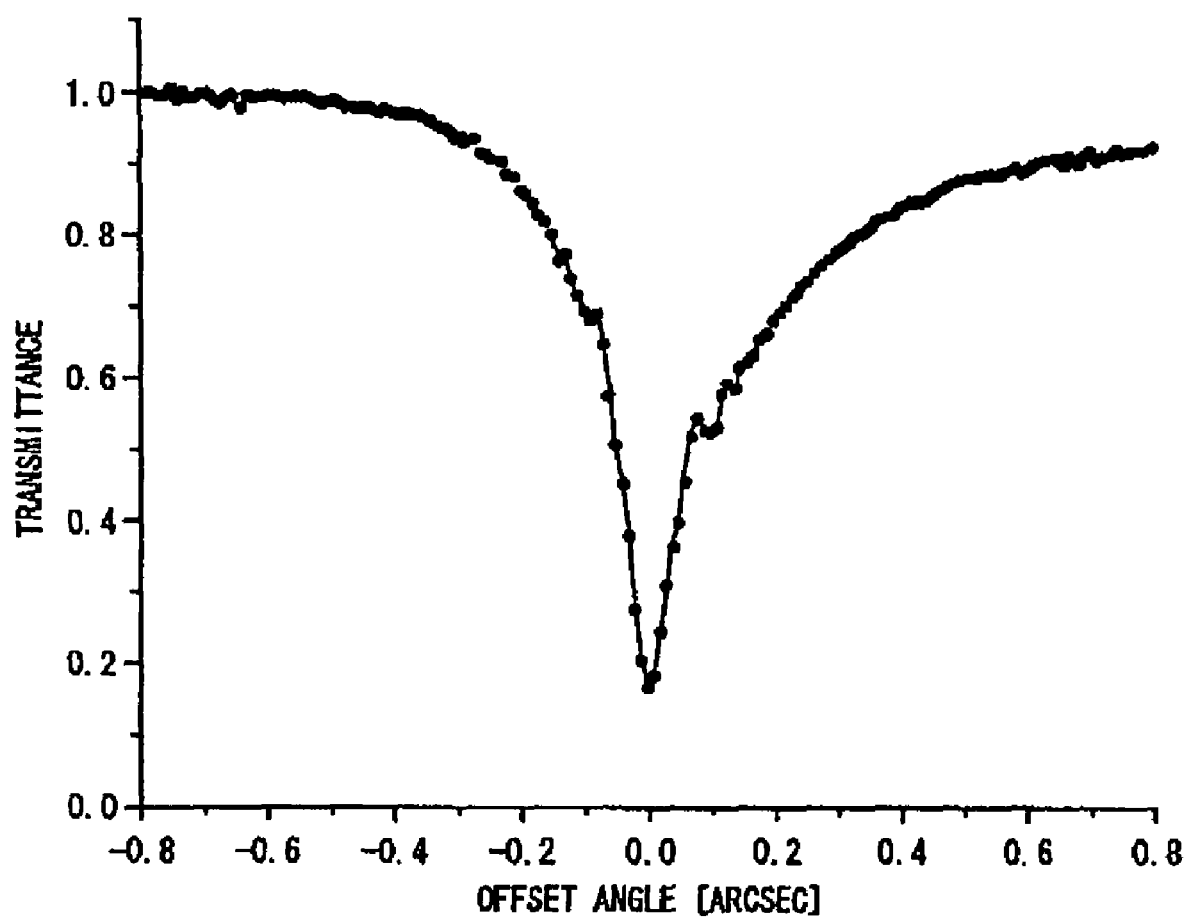
FIG. 10 is a view showing the transmittance curve of the transmission-type angle analyzer.

The transmittance curve of the transmission-type angle analyzer 20 is shown in FIG. 10. An offset angle at which the angle analyzer 201 with the direction perpendicular to the X-ray beam is set so that the transmittance becomes one. The refracted X-ray beam 22 and transmitted X-ray beam 24 are emitted from the angle analyzer 20. A CCD camera 16 receives the refracted X-ray beam 22. In this case, a dark field image is taken in the CCD camera 16.

The output data from the CCD camera 16 is input into a computer 18. The CT-reconstruction process is the same as that in the embodiment 1. The method for constructing a 3-dimensional image is conducted according to the following steps.
(1) The sample 12 is set.
(2) The refracted X-ray beam through the sample 12 is transmitted through the angle analyzer 20 and is incident on the CCD camera 16. The refracted angle data from the CCD camera 16 is inputted into the computer 18.
(3) The sample is rotated to a subsequent angle, and the step (2) is carried out.
(4) The same operations are continued until the rotating angle of the sample is reached 180°.
(5) The image is extracted due to the Filtered Backprojection method by utilizing the equation (4).

In the step (4), the axis at which the sample 12 is rotated is perpendicular to the image plane of FIG. 9, while any rotational axis may be selected.

As described in the embodiments 1 and 2, the problems in the CT-reconstruction based on a refraction contrast are solved successfully. The theory described above serves as a basis for the programming algorithm prepared and tested in the embodiments. It has been proved that the result of reconstruction is reliable.

INDUSTRIAL APPLICABILITY

The 3-dimensional image construction method and apparatus in accordance with the present invention may be utilized for an X-ray pathological diagnosis and contribute to the progress thereof.

The invention claimed is:

1. An apparatus for constructing a 3-dimensional image of an object, comprising:
generating means for generating a monochromatic and parallel X-ray beam from an X-ray beam;
a reflection-type angle analyzer for reflecting the monochromatic and parallel X-ray beam at reflecting points on both slopes of a reflection curve of the reflection-type angle analyzer, angle information being extracted to a maximum extent at the reflecting points, the monochromatic and parallel X-ray beam including an X-ray beam that passed through the object when the object is positioned rotatably in the monochromatic and parallel X-ray beam and an X-ray beam from the generating means when the object is not positioned in the monochromatic and parallel X-ray beam;
an imaging device for generating a refraction angle data by receiving the monochromatic and parallel X-ray beam reflected on the reflection-type angle analyzer to detect the intensity thereof and output a refraction angle data; and
an arithmetic device for constructing the 3-dimensional image by carrying out an arithmetical operation for the refraction angle data from the imaging device; wherein
the arithmetic device extracts, from the refraction angle data, a refraction angle distribution $\Delta\alpha(\Theta, t)$, wherein $\Theta$ is a rotation angle of the object and t is a projection coordinate perpendicular to the X-ray beam, and reconstructs a refraction index gradient $\nabla\tilde{n}$ from the extracted refraction angle distribution $\Delta\alpha(\Theta, t)$, and the reconstruction of the refraction index gradient $\nabla\tilde{n}$ is carried out by an algorithm $$\Delta\alpha(\Theta,t)e^{i\Theta} = \int_S |\nabla\tilde{n}(r)| e^{i\phi(r)} dr$$

wherein $\tilde{n}(r)$ is a local refraction index which has a relation to the refraction index $n(r)$ in portion r as $\tilde{n}=1-n$, $\phi(r)$ is the angle between the direction of the X-ray beam and the refraction index gradient $\nabla\tilde{n}(r)$, and S is an integration path.

2. An apparatus for constructing a 3-dimensional image of an object according to claim 1, wherein the arithmetic device converts the reconstructed refraction index gradient $\nabla\tilde{n}$ to a scalar field $\tilde{n}(r)$.

3. An apparatus for constructing a 3-dimensional image of an object according to claim 2, wherein the arithmetic device forms a plurality of 2-dimensional slice images of the object in the form of the scalar field $\tilde{n}$ and construct the 3-dimensional image by reconstructing the plurality of 2-dimensional slice images.

4. An apparatus for constructing a 3-dimensional image of an object according to claim 2, wherein the generating means is a monochromator, and the imaging device is a CCD camera.

5. An apparatus for constructing a 3-dimensional image of an object according to claim 1, wherein the generating means is a monochromator, and the imaging device is a CCD camera.

6. An apparatus for constructing a 3-dimensional image of an object, comprising:
generating means for generating a monochromatic and parallel X-ray beam from an X-ray beam;
a transmission-type angle analyzer for transmitting the monochromatic and parallel X-ray beam passed through the object positioned rotatably in the monochromatic and parallel X-ray beam;
an imaging device for generating a refraction angle data by receiving the monochromatic and parallel X-ray beam that passed through the transmission-type angle analyzer to detect the intensity thereof and output a refraction angle data; and an arithmetic device for constructing the 3-dimensional image by carrying out an arithmetical operation for the refraction angle data from the imaging device; wherein the arithmetic device extracts, from the refracted angle data, a refraction angle distribution $\Delta\alpha(\Theta, t)$, wherein $\Theta$ is a rotation angle of the object and t is a projection coordinate perpendicular to the X-ray beam, and reconstructs a refraction index gradient $\nabla\tilde{n}$ from the extracted refraction angle distribution $\Delta\alpha(\Theta, t)$, and the reconstruction of the refraction index gradient $\nabla\tilde{n}$ is carried out by an algorithm $$\Delta\alpha(\Theta,t)e^{i\Theta}=\int_S|\nabla\tilde{n}(r)|e^{i\phi(r)}dr$$

wherein $\tilde{n}(r)$ is a local refraction index which has a relation to the refraction index $n(r)$ in portion r as $\tilde{n}=1-n$, $\phi(r)$ is the angle between the direction of the X-ray beam and the refraction index gradient $\nabla\tilde{n}(r)$, and S is an integration path.

7. An apparatus for constructing a 3-dimensional image of an object according to claim 6, wherein the arithmetic device converts the reconstructed refraction index gradient $\nabla\tilde{n}$ to a scalar field $\tilde{n}(r)$.

8. An apparatus for constructing a 3-dimensional image of an object according to claim 7, wherein the generating means is a monochromator, and the imaging device is a CCD camera.

9. An apparatus for constructing a 3-dimensional image of an object according to claim 6, wherein the generating means is a monochromator, and the imaging device is a CCD camera.

10. A method for constructing a 3-dimensional image of an object, comprising the steps of:

generating a monochromatic and parallel X-ray beam by a monochromator;

receiving a first monochromatic and parallel X-ray beam passed through the object and reflected on a reflective type angle analyzer at a first reflective angular position, on a left side slope of a rocking curve of the reflective type angle analyzer by means of an imaging device;

receiving a second monochromatic and parallel X-ray beam passed through the object and reflected on the reflective type angle analyzer at a second reflective angular position on a right side slope of the rocking curve of the reflective type angle analyzer by means of the imaging device;

extracting a refraction angle from the first X-ray beam and the second X-ray beam; and constructing the 3-dimensional image by carrying out an arithmetical operation for the refraction angle data from the imaging device; wherein the arithmetical operation includes the steps of, extracting a refraction angle distribution $\Delta\alpha(\Theta, t)$, wherein $\Theta$ is a rotation angle of the object and t is a projection coordinate perpendicular to the X-ray beam, reconstructing a refraction index gradient $\nabla\tilde{n}$ from the refraction angle distribution $\Delta\alpha(\Theta, t)$, and converting the reconstructed refraction index gradient $\nabla\tilde{n}$ to a field $\tilde{n}(r)$.

11. A method for constructing a 3-dimensional image of an object according to claim 10, wherein the reconstruction of the refraction index gradient $\nabla\tilde{n}$ from the refraction angle distribution $\Delta\alpha(\Theta, t)$ is carried out by an algorithm $$\Delta\alpha(\Theta,t)e^{i\Theta}=\int_S|\nabla\tilde{n}(r)|e^{i\phi(r)}dr$$

wherein $\tilde{n}(r)$ is a local refraction index which has a relation to the refraction index $n(r)$ in portion r as $\tilde{n}=1-n$, $\phi(r)$ is the angle between the direction of the X-ray beam and the refraction index gradient $\nabla\tilde{n}(r)$, and S is an integration path.

12. A method for constructing a 3-dimensional image of an object according to claim 11, further comprising:

forming a plurality of 2-dimensional slice images of the object in the form of the scalar field $\tilde{n}$; and constructing the 3-dimensional image by reconstructing the plurality of 2-dimensional slice images.

13. A method for constructing a 3-dimensional image of an object, comprising the steps of:

generating a monochromatic and parallel X-ray beams from an X-ray beam by a monochromator;

transmitting, through a transmission-type angle analyzer, the monochromatic and parallel X-ray beam that passed through the object positioned rotatably in the monochromatic and parallel X-ray beam, and receiving the monochromatic and parallel X-ray beam that passed through the transmission-type angle analyzer by an imaging device to acquire a refraction angle data; and constructing the 3-dimensional image by carrying out an arithmetical operation for the refraction angle data from the imaging device; wherein the arithmetical operation includes the steps of, extracting a refraction angle distribution $\Delta\alpha(\Theta, t)$, wherein $\Theta$ is a rotation angle of the object and t is a projection coordinate perpendicular to the X-ray beam, reconstructing a refraction index gradient $\nabla\tilde{n}$ from the refraction angle distribution $\Delta\alpha(\Theta, t)$, converting the reconstructed refraction index gradient $\nabla\tilde{n}$ to a scalar field $\tilde{n}(r)$, and wherein the reconstruction of the refraction index gradient $\nabla\tilde{n}$ from the refraction angle distribution $\Delta\alpha(\Theta,t)$ is carried out by an algorithm $$\Delta\alpha(\Theta, t)e^{i\Theta}=\int_S|\nabla\tilde{n}(r)|e^{i\phi(r)}dr$$

wherein $\tilde{n}(r)$ is a local refraction index which has a relation to the refraction index $n(r)$ in portion r as $\tilde{n}=1-n$, $\phi(r)$ is the angle between the direction of the X-ray beam and the refraction index gradient $\nabla\tilde{n}(r)$, and S is an integration path.

* * * * *